United States Patent [19]

Kiniwa et al.

[11] Patent Number: 5,173,421

[45] Date of Patent: Dec. 22, 1992

[54] CELL CULTURE CARRIERS

[75] Inventors: Hideaki Kiniwa; Hirohisa Kubota, both of Yokohama, Japan

[73] Assignee: Mitsubishi Kasei Corporation, Tokyo, Japan

[21] Appl. No.: 448,969

[22] Filed: Dec. 12, 1989

[30] Foreign Application Priority Data

Dec. 14, 1988 [JP] Japan .................. 63-315518
May 2, 1989 [JP] Japan .................. 1-113084

[51] Int. Cl.$^5$ ................ C12N 5/00; C12N 11/02
[52] U.S. Cl. .................. 435/240.243; 435/240.23; 435/240.24; 435/180
[58] Field of Search ............ 435/240.23, 240.24, 435/240.25, 240.243, 180

[56] References Cited

U.S. PATENT DOCUMENTS 3,910,819 10/1975 Rembaum et al. .......... 435/240.243
4,415,668 11/1983 Siegel ..................... 435/240.24
4,861,714 8/1989 Dean, Jr. et al. ........... 435/240.23

FOREIGN PATENT DOCUMENTS 226282 9/1988 Japan .

OTHER PUBLICATIONS

Lazar, et al., in Modern Approaches to Animal Cell Technology Spier, et al. (Eds) CH. 30, pp. 437–448 Butterworth & Co. Ltd. 1987.
Arye Lazer et al., Cytotechnology (1988).
Chemical Abstracts, vol. 103, No. 19 Nov. 11, 1985; Columbus, Ohio Japanese read cross society: "Artificial interferon production inducers" & JP-A-6070098, Apr. 20, 1985 p. 587; right-hand column; ref No. 159135.
Patent Abstracts of Japan; vol. 13, No. 21 (C-560) (3369) Jan. 18, 1989, & JP-A-63 226282 (Mitsubishi Kasei Corp.) Sep. 20, 1988.
The Proceedings of Biotech 84 Europe vol. 1 Europe 1984, pp. 343-354; SaU1 Reuveny et al., "Newly developed microcarrier culturing systems an overvidw" pp. 347-350.

Primary Examiner—John J. Doll
Assistant Examiner—George C. Elliott
Attorney, Agent, or Firm—Oblon, Spivak, McClelland, Maier & Neustadt

[57] ABSTRACT

This invention relates to cell culture carriers consisting of a porous support, at least a part of which surface being coated with a water-insoluble polymer constituted by (meth)acrylic acid ester and/or (meth)acrylamides and a cross-linking agent, and having a positively chargeable chemical moiety on the polymer surface. The present carriers have enabled the high-density cell culture in any type of the culture methods.

20 Claims, No Drawings

CELL CULTURE CARRIERS

BACKGROUND OF THE INVENTION

1. Field of the Invention

This invention relates to cell culture carriers and a method for the culture of cells, particularly to the cell culture carriers suitable for use in high-density culture of anchorage-dependent cells and the method for the cell culture by using said carriers.

2. Description of the Prior Art

There are many known methods for the cell culture in large quantity and in high-density, such as those using microcapsule, hollow fiber, ceramic carriers, microcarriers and glass beads.

With the recent progress in methodology of the cell culture, however, it has become necessary to develop cell culture carriers and methods for the cell culture which allow the cell culture in much higher density than before. Since carriers such as microcarriers and glass beads, in which cells can anchor or adhere only to the surface of the carriers, have a low surface area per a unit of volume (hereinafter referred to as "a S/V value"), they cannot be advantageously used in the high-density cell culture.

For the purpose of enabling such high-density cell culture, there have been proposed a few kinds of cell culture carriers whose inner surface may also serve as the surface to which cells can adhere, i.e., as "an anchorage area."

Japanese Patent Application Laying Open (KOKAI) No. 502936/87 and Bio/technology, Vol. 5, pp. 835–837, 1987 (Verax Corporation) disclose spherical carriers made of three-dimensionally woven collagen fiber, which, however, cannot be subjected to sterilization by an autoclave.

Japanese Patent Application Laying Open (KOKAI) No. 169837/87 and Bio/technology, Vol. 4, pp. 989–990 (1987) refer to possibility of the high-density cell culture by using porous gelatin carriers. The porous gelatin carriers may be sterilized by a autoclave, but even highly anchorage-dependent cells can hardly adhere to them, requiring a special adhering technique.

G. A. Pkhakadze reports in Ukr. Biokhim. Zh., Vol.51, 4. pp. 355–362 (1979) that rat fibroblasts can be cultured with polyurethane carriers.

Japanese Patent Application Laying Open (KOKAI) No. 215386/87 discloses possibility of the high-density cell culture by using polyurethane foam carriers. However, cells can hardly adhere to such carriers. Even if they are attached to said carriers, they proliferate very slowly and detach therefrom very easily. Furthermore, protein or virus secreted from the attached cells will likely be adsorbed by the carriers. Watabe et al. reports that materials eluted from polyurethane deteriorate the development of culture cells (Reports of the institute for medical and dental engineering, Tokyo Medical and Dental University, Vol. 10, pp. 69–75 (1976)).

The inventors of the present application have previously disclosed, in Japanese Patent Applications Laying Open (KOKAI) No. 71173/88, No. 226282/88 and 10979/89, cell microcarriers consisting of water-insoluble polymer particles constituted by (meth)acrylic acid ester and having a positively chargeable chemical moiety or protein, which is chemically bound to their surface. However, since the anchorage area of the particles with a low S/V value was restricted only to their outer surface, the above cell microcarriers could not sufficiently provide the high-density cell culture, as mentioned above.

Accordingly, there has been a great demand for cell carriers which can attach and grow cells well and can be sterilized by an autoclave.

SUMMARY OF THE INVENTION

The present inventors have found that by coating or soaking a porous support with (meth)acrylic acid ester and/or (meth)acrylamides and a cross-linking agent followed by polymerization in situ, it is possible to obtain cell culture carriers which have a high S/V value, suitable average pore size and density and, accordingly, allow good attachment and growth of the cells with little possibility of nonspecifically adsorbing biologically active substance such as protein.

An aspect of the present invention is to provide cell culture carriers consisting of a porous support, at least a part of which surface being coated with a water-insoluble polymer constituted by (meth)acrylic acid ester and/or (meth)acrylamides and a cross-linking agent, and having a positively chargeable chemical moiety on the polymer surface.

DETAILED DESCRIPTION OF THE INVENTION

The requirements to be met by cell culture carriers in order to efficiently grow cells, in particular the anchorage-dependent cells, and to efficiently recover the biologically active substance secreted by the culture cells may be as follows:

(a) the cells may easily adhere to the carriers;
(b) the carriers have a high S/V value;
(c) the carriers have such a suitable pore size as a culture medium may pass through them; and
(d) the carriers are so constructed as to inhibit as much as possible the culture cells from being subjected to shearing force.

For fulfilling the above requirements, a porous support according to the present invention should have an average pore size of preferably from 10 $\mu$m to 500 $\mu$m, more preferably from 20 $\mu$m to 100 $\mu$m. It should also have porosity of preferably from 40 to 99%, more preferably from 60 to 95% by volume. In the present invention, the average pore size is determined after magnification ($\times 50 - \times 200$) by Nikon Profile Projector V-12 (NIKON CORPORATION, JAPAN). If the pore size is too small, it will be very difficult to coat an inner part of the pore with the water-insoluble polymer and to provide the cell culture carriers having uniform cell-adsorbing property. Furthermore, the culture cells can hardly move through such small pore, and the inner part of the pore cannot be efficiently utilized. If the pore size, on the contrary, is too large, the support may often lack sufficient mechanical strength.

Cell density of the anchorage-dependent cells in culture is generally proportional to a value of the anchorage area per a unit of volume. It is therefore preferable to use a support with the value as large as possible for attaining the high-density culture.

Materials suitable for the support according to the present invention include those having good affinity for monomer component of the above water-insoluble polymer, the cross-linking agent and a diluent and having resistance against a solution thereof. It is further desirable that the materials should resist sterilization treatment by, for example, auto-claving (e.g., 121° C. for 30 min), ethyleneoxide gas and gamma ray.

It is also preferable that the support materials never or almost never adsorb the biologically active substance and that they are not subjected to deformation, chemical or biological autolysis or elution of the component thereof during the culture.

The materials for use in the present porous support may include the following:

(a) polymer foam such as urethane foams, ether foams and ester foams;
(b) porous ceramics such as silica and alumina;
(c) cloth such as non-woven fabric;
(d) wood;
(e) porous glass beads; and
(f) porous metals.

Among them, polymer foams, particularly polyurethane foam, are economical and have the advantages such as a long radius of curvature of the anchorage area, optical transparency, and chemical and biological stability. The size of the urethane foam generally ranges from $10^{-7}$ to $10^{-6}$ cm$^3$.

The size of the support according to the present invention may widely vary depending on its average pore size, the side thereof being preferably 100 μm−5 mm, more preferably 100 μm−700 μm, when used for culture in a fluid condition such as suspended culture, recurrent culture, fluidized bed culture or rotary culture. Beyond this range, the culture medium could not sufficiently diffuse into the inner part of the support, and the anchorage area on the inner surface would not be efficiently utilized. The average pore size of the support of this type ranges preferably from 10 μm to 200 μm. The support is made preferably of polyurethane in view of the inner diffusion. Furthermore, the support takes preferably a spherical shape in order to diffuse uniformly into the inner most-possible part thereof to decrease its apparent viscosity in the culture medium and to avoid damage on cells caused by collision among the supports as much as possible.

On the other hand, when the support is used as an immobilized bed, its size normally ranges from 5 to 103 cm3, which may be adjusted by cutting in accordance with a scale of a culture vessel. The average pore size of the support in this case is preferably larger than that of the support used in the fluid condition, generally from 500 um to 3 mm, wherein the culture medium may diffuse well into the inner part of the support.

The present support may also be used for culturing suspended cells such as hybridomas and protoplasts. In this case, it is preferable that its average pore size is relatively small, ranging from 10 to 100 μm.

Density of the support of the present invention, generally from 1.00 to 1.40 g/ml, may vary widely depending on the content of monomer and the method of culture.

When culturing anchorage-dependent cells, the present support preferably has a communicating-pore structure. The support made of polyurethane foam may take either the communicating-pore structure or a semi-communicating pore structure. In the latter a skeleton is suitably divided by membranes, so long as polyurethane foam has a three-dimensional skeleton structure. However, for obtaining a high S/V value such as, for example, 20 to 1,000 cm$^2$/ml or more of polyurethane, the semi communicating-pore structure is preferable.

The water-insoluble polymer which coats the surface of the porous support may be prepared by co-polymerizing (meth)acrylic acid ester and/or (meth)acrylamides (both hereinafter referred to as "a polymeric monomer") with the cross-linking agent.

(Meth)acrylic acid ester having a CLOGP value of −1.5 to +2.0 is preferable, which may include 2-hydroxyethyl (meth)acrylate, diethyleneglycol (meth)acrylate, triethyleneglycol (meth)acrylate, tetraethyleneglycol (meth)acrylate, octaethyleneglycol (meth)acrylate, polyethyleneglycol (meth)acrylate, glycerol (meth)acrylate, glycidyl (meth)acrylate and monomers listed in TABLE 1 below.

(Meth)acrylamides having the CLOGP value of −1.0 to +2.0 are preferable, which may include (meth)acrylamide, N-hydroxyethyl (meth)acrylamide, N-diethyleneglycol (meth)acrylamide, N-polyethyleneglycol (meth)acrylamide, N-hydroxypropyl (meth)acrylamide, methyl (meth)acrylamide and monomers listed in TABLE 2 below.

In TABLES, "Me" and "Et" mean methyl and ethyl groups, respectively. The CLOGP value is a logarithm of partition coefficient of a solute between 1-octanol and water.

The CLOGP value was proposed by Pomona College (California, USA) (cf. a program of FACOM 3.33 version edited by T. Nishioka, Kyoto University). It has made it possible to quantitatively show the hydrophobicity of a neutral molecule.

The cross-linking agent may be optionally added to the above polymeric monomers. A suitable cross-linking agent may be a polyfunctional vinyl monomer which can be co-polymerized with the above polymeric monomer and is as highly hydrophilic as possible. A preferable CLOGP value of the agent is in the range of from −1.5 to +2.5. Examples of such cross-linking agent are ethyleneglycol di(meth)acrylate, diethyleneglycol di(meth)acrylate, triethyleneglycol di(meth)acrylate, tetraethylenglycol di(meth)acrylate, octaethyleneglycol di(meth)acrylate, polyethyleneglycol di(meth)acrylate, glycerol di(meth)acrylate, methylene bis(meth)acrylamide, ethylene bis(meth)acrylamide, and diethylene bis(meth)acrylamide. The cross-linking agent can prevent leakage of soluble components from the support or water-insoluble polymer coating, and exfoliation of the polymer coating from the support. If the content of the cross-linking agent is too high, the polymer coating will adsorb the biologically active substance secreted by the culture cells and proteins in serum, making it impossible to efficiently recover them. Accordingly, the content of units derived from the cross linking agent ranges preferably from 1 to 50%, more preferably from 2 to 20% by weight of the water-insoluble polymer.

A diluent may be preferably added to the polymeric monomers and the cross-linking agent so that the polymeric monomers and cross-linking agent may penetrate and uniformly coat the porous support. The added diluent could further provide the polymer with a suitable flexibility.

Any compound which may dissolve the polymeric monomers and is inactive to functional groups of the same monomers, such as methacryloyl, hydroxyl, glycidyl, amide and amino as well as to the porous support can be used as the diluent in the present invention. A preferable diluent includes, depending on the polymeric monomers to be used, benzene, toluene, methyliosbutyl ketone, ethyl acetate, butyl acetate, 1-hexanol, cyclohexanol, heptanol, octanol, cyclohexanone, dibutylether, tetrahydrofuran, 1,2-dichloroethane, 1,4-dioxane, chloroform, carbon tetrachloride, dimethyl formamide, dimethylsulfoxide, acetonitrile, ethanol, propanol, methanol, acetone and a mixture thereof with water.

For obtaining many contact points between cells and the polymer coating, it is generally preferable that the water-insoluble polymer for coating is in the form of a non-porous coating, while not excluding a finely porous coating. When a good solvent for the polymeric monomers is used as the diluent, the resulting non-soluble polymer coating will be optically transparent, and a poor solvent will contrary result in an opaque porous polymer coating. More hydrophilic monomer or cross-linking agent could also form the optically transparent polymer coating.

The diluent may be added preferably in 0-10 times, more preferably 1.0-4.0 times by weight the total amount of the polymeric monomers. An excess amount of the diluent would result in reduction of polymerization yield as well as exfoliation of the polymer coating from the support.

For attachment, spreading and growth of cells, a charge capacity of the positively chargeable chemical moiety according to the present invention ranges preferably from 0.5 to 3.5 meq/g in the culture medium.

Similarly, the CLOGP value of the monomers which have the positively chargeable chemical moiety in the water-insoluble polymer is also an important factor for the spreading and growth of cells. Though some of the positively chargeable chemical moieties are believed to dissociate in the culture medium, it has been reported that a net charge capacity may hardly or irregularly affect a growth rate at pH 7.20 (W. S. Hu et al., Biotechnology and Bioengineering, Vol. 29, pp. 1155-1163, 1987).

Accordingly, the CLOGP value should be taken into account in determining hydrophobicity of the polymeric monomer having the, positively chargeable chemical moiety in the resulting polymer. The CLOGP value of the above polymeric monomers is preferably of from $-2.0$ to $.2.0$, more preferably of from $-1.5$ to $+2.0$. The CLOGP value under $-2.0$, in general, would adversely affect the attachment of cells. The CLOGP value over $+2.0$, on the other hand, would deteriorate the spreading and growth of cells, and further cause the adsorption of the biologically active substance secreted by the culture cells onto the culture carriers. The present inventors call this phenomenon "hydrophobic inhibition." Furthermore, it is preferred that the monomer with a lower CLOGP value should be used in a larger amount in order to obtain the good distensibility and growability of cells. The monomers listed in TABLES 1 and 2 have the CLOGP value in a range of from $-2.0$ to $.2.0$.

For example, the preferable monomers which have the positively chargeable chemical moiety are N,N-diethylaminoethyl (meth)acrylate, N,N-diethylaminopropyl (meth)acrylate, N,N-dimethylaminoethyl (meth)acrylate, 2-hydroxyethylamino-2-hydroxypropyl (meth)acrylate, 3-hydroxypropylamino-2-hydroxypropyl (meth)acrylate, 4-hydroxybutylamino-2-hydroxypropyl (meth)acrylate, N,N-diethylamino-2-hydroxypropyl (meth)acrylate, N-methylhydroxyethylamino-2-hydroxypropyl (meth)acrylate, N,N-diethylaminoethylamino-2-hydroxypropyl (meth)acrylate, 2-mercaptoethylamino-2-hydroxypropyl (meth)acrylate, 2-aminoethylamino-2-hydroxypropyl (meth)acrylate, 3-aminopropylamino-2-hydroxypropyl (meth)acrylate, 4-aminobutylamino-2-hydroxypropyl (meth)acrylate, trimethylammonium-2-hydroxypropyl (meth)acrylate, aminoethylacrylamide, dimethylaminoethylacrylamide, diethylaminoethylacrylamide, dimethylaminopropylacrylamide and trimethylaminoethylacrylamide.

The positively chargeable chemical moiety may be either previously incorporated in the polymeric monomer, or introduced into the resulting polymer.

At least a part or all, if possible, of the surface of the porous support may be coated with the water-insoluble polymer in the following manner.

A polymerization initiator is added to a monomer solution consisting of the polymeric monomer and cross-linking agent, and diluent if desired. The porous support is then soaked in the monomer solution. After pressing and squeezing the porous support so as to remove an excess of the monomer solution, the monomer is allowed to be polymerized in nitrogen atmosphere. When the carriers for use in the immobilized beds are prepared, the porous support will be cut before polymerization into a small piece with a side below 10 cm, or adjusted to the shape of the culture vessel as much as possible in order to be uniformly soaked in the solution and coated therewith. In such a case, centrifugation may be used for removing the excess monomer solution. If the porous support is relatively small, the above operation may be carried out after being packed in a column. It is noted in the above procedure that the monomer solution should not pool in the support during the removal of the excess monomer solution. An amount of the coating may be preferably from 0.5-20% of the total cell culture carriers' weight Suitable polymerization initiators include peroxides such as benzoyl peroxide, lauroyl peroxide and acetyl peroxide, azo compounds such as 2,2'-azobis-2-2-cyclopropylpropyonitrile, and those for use in a polymerization at a very low temperature, such as hydrogen peroxide - $Fe^{2+}$ salt, peroxide salt - sodium hydrogensulfate, triethyl boron and diethyl zinc.

The polymerization initiator may be selected depending on the monomer, cross-linking agent and diluent to be used. When the monomer solution is water-soluble, it is preferable to use redox initiators, water-soluble azo compounds, ammonium peroxide, potassium peroxide - N,N,N',N'- tetramethylethylenediamine. When the monomer solution is hardly soluble in water, peroxides and azo compounds are preferably used.

It is generally preferred that the redox initiators are used at 0° C.-50° C., and the azo compounds and peroxides are used at 30° C.-100° C.

If the polymeric monomers have no positively chargeable chemical moiety or its charge capacity is insufficient, such moiety may be introduced into the resulting polymer. For example, the glycidyl group in the polymer may be modified by amines so as to form the positively chargeable chemical moiety. The hydroxyl or 2,3-dihydroxypropyl group may be reacted with cyagen bromide to give imidocarbonate which will in turn react with diamine and generate the positively chargeable chemical moiety. Alternatively, they may be reacted with trichlorotriazine to give a dichlorotriacyl group which will in turn react with diamine to generate the positively chargeable chemical moiety.

It is often very difficult to determine the charge capacity of the support. In such a case, after the monomers are polymerized in a petri dish, the positive charge capacity of the recovered polymer can be estimated by titration. The charge capacity of the porous support is preferably from 0.2 to 4.0 meq, more preferably from 0.7 to 2.0 meq per gram of the water-insoluble polymer. The charge capacity represented in EXAMPLES was measured by this method.

The type of the culture method using the present cell culture carriers depends, for example, on a scale and purpose of the culture. There may be exemplified a stationary culture using a petri dish or T-flask, suspended culture using a spinner flask or roller bottle, the immobilized bed culture and continuous culture using an air lift. The present cell culture carriers may be used preferably in an amount of 5-60% by volume of the culture medium in accordance with the culture method.

TABLE 1

| (meth)acrylic acid ester | CLOGP (R = H) | CLOGP (R = Me) |
|---|---|---|
| $CH_2=CR-C(O)-O-CH_2-CH_2-N(Me)_2$ | 0.814 | 1.123 |
| $CH_2=CR-C(O)-O-CH_2-CH_2-CH_2-N(Me)_2$ | 0.470 | 0.779 |
| $CH_2=CR-C(O)-O-CH_2-CH_2-N(Et)_2$ | 1.712 | 1.981 |
| $CH_2=CR-C(O)-O-CH_2-CH_2-CH_2-N(Et)_2$ | 1.368 | 1.677 |
| $CH_2=CR-C(O)-O-CH_2-CH(OH)-CH_2-NH_2$ | −0.810 | −0.510 |
| $CH_2=CR-C(O)-O-CH_2-CH(OH)-CH_2-N(Et)_2$ | 0.807 | 1.116 |
| $CH_2=CR-C(O)-O-CH_2-CH(OH)-CH_2-NH-CH_2-CH_2-OH$ | −0.978 | −0.669 |
| $CH_2=CR-C(O)-O-CH_2-CH(OH)-CH_2-NH-CH_2-CH_2-CH_2-OH$ | −1.434 | −1.125 |
| $CH_2=CR-C(O)-O-CH_2-CH(OH)-CH_2-NH-(CH_2)_4-OH$ | −0.905 | −0.596 |
| $CH_2=CR-C(O)-O-CH_2-CH(OH)-CH_2-N(Me)-CH_2-CH_2-OH$ | −0.636 | −0.327 |
| $CH_2=CR-C(O)-O-CH_2-CH(OH)-CH_2-N(Et)-CH_2-CH_2-OH$ | −0.187 | 0.122 |
| $CH_2=CR-C(O)-O-CH_2-CH(OH)-CH_2-N(\text{piperazinyl})-N-H$ | −0.353 | −0.044 |
| $CH_2=CR-C(O)-O-CH_2-CH(OH)-CH_2-NH-C_6H_5$ | 1.363 | 1.674 |
| $CH_2=CR-C(O)-O-CH_2-CH(OH)-CH_2-NH-CH_2-CH_2-NH_2$ | −0.904 | −0.595 |
| $CH_2=CR-C(O)-O-CH_2-CH(OH)-CH_2-NH-(CH_2)_3-NH_2$ | −1.334 | −1.075 |

TABLE 1-continued

| (meth)acrylic acid ester | CLOGP (R = H) | CLOGP (R = Me) |
|---|---|---|
| $CH_2=\overset{R}{\underset{\phantom{x}}{C}}-\overset{O}{\underset{\phantom{x}}{C}}-O-CH_2-\overset{OH}{\underset{\phantom{x}}{CH}}-CH_2-NH-(CH_2)_4-NH_2$ | −0.805 | −0.496 |
| $CH_2=\overset{R}{\underset{\phantom{x}}{C}}-\overset{O}{\underset{\phantom{x}}{C}}-O-CH_2-\overset{OH}{\underset{\phantom{x}}{CH}}-CH_2-NH-(CH_2)_6-NH_2$ | 0.253 | 0.562 |
| $CH_2=\overset{R}{\underset{\phantom{x}}{C}}-\overset{O}{\underset{\phantom{x}}{C}}-O-CH_2-\overset{OH}{\underset{\phantom{x}}{CH}}-CH_2-NH-CH_2-CH_2-SH$ | 0.066 | 0.375 |

TABLE 2

| (meth)acrylamide | CLOGP (R = H) | CLOGP (R = Me) |
|---|---|---|
| $CH_2=\overset{R}{\underset{\phantom{x}}{C}}-\overset{O}{\underset{\phantom{x}}{C}}-NH-CH_2-CH_2-NH_2$ | −1.013 | −0.508 |
| $CH_2=\overset{R}{\underset{\phantom{x}}{C}}-\overset{O}{\underset{\phantom{x}}{C}}-\underset{H}{\underset{\phantom{x}}{N}}-CH_2-CH_2-N(Me)(Me)$ | −0.215 | 0.290 |
| $CH_2=\overset{R}{\underset{\phantom{x}}{C}}-\overset{O}{\underset{\phantom{x}}{C}}-\underset{H}{\underset{\phantom{x}}{N}}-CH_2-CH_2-N(Et)(Et)$ | −0.683 | 1.188 |
| $CH_2=\overset{R}{\underset{\phantom{x}}{C}}-\overset{O}{\underset{\phantom{x}}{C}}-\underset{H}{\underset{\phantom{x}}{N}}-CH_2-CH_2-CH_2-N(Me)(Me)$ | −0.920 | −0.611 |
| $CH_2=\overset{R}{\underset{\phantom{x}}{C}}-\overset{O}{\underset{\phantom{x}}{C}}-\underset{H}{\underset{\phantom{x}}{N}}-CH_2-CH_2-CH_2-N(Et)(Et)$ | −0.022 | 0.287 |
| $CH_2=\overset{R}{\underset{\phantom{x}}{C}}-\overset{O}{\underset{\phantom{x}}{C}}-\underset{H}{\underset{\phantom{x}}{N}}-CH_2-CH_2-NH-\underset{Me}{\overset{Me}{C}}-Me$ | 0.529 | 0.838 |

EXAMPLE 1

A monomer solution was prepared by mixing polyethyleneglycol methacrylate (Blenmer PE-200; Nippon Oil and Fats Co., Ltd.) 5.10 g, glycidyl methacrylate 2.50 g, polyethyleneglycol dimethacrylate (4G, Shin-Nakamura Chemicals, Co., Ltd.) 2.40 g, 1,4-dioxane 20.0 g, and an azo compound initiator V-70 (2,2'-azobis(4-methoxy-2,4-valeronitrile); WAKO Pharmaceuticals Co.) 20 mg dissolved in methylene chloride 0.5 ml. By introducing nitrogen gas into the solution at a room temperature, dissolved oxygen in the solution was removed out.

A polyurethane foam piece (an average pore size of 250 μm, semi-communicating pore structure; MD Kasei Co.; 10 cm × 10 cm × 7 cm, 700 cm$^3$) was soaked in the monomer solution and an excess amount of the solution was removed from the polyurethane foam by pressing and squeezing. The polyurethane foam piece was then applied into a glass vessel and allowed to stand under nitrogen atmosphere at 50° C. for 2 hrs. for polymerization. The resulting polymer was washed with 50% acetone aqueous solution (50° C.) and then with distilled water for removing the remaining monomer and dioxane.

After replacing the distilled water by dioxane, dioxane solution 10 ml containing 2.0 g of ethanolamine was added dropwise to the piece and incubated for aminolysis at 75° C. for 4 hrs. After the completion of the reaction, the polyurethane foam piece was thoroughly washed with 50% acetone aqueous solution and then with distilled water. An amount of the coating polymer was 12.5% by weight.

The monomer unit having the positively chargeable chemical moiety in the above polymer was methacrylic acid-2-hydroxyethylamino-2-hydroxypropyl with the CLOGP value of −0.669. Its estimated charge capacity, S/V value and porosity were about 1.71 meq/g, 52 cm$^2$/ml and about 87%, respectively.

EXAMPLE 2

A monomer solution was prepared by mixing polyethyleneglycol methacrylate (Blenmer PE-350; Nippon Oil and Fats Co., Ltd.) 5.0 g, glycidyl methacrylate 2.60 g, glycerol dimethacrylate 1.40 g, 1,4-dioxane 20.0 g, and the initiator V-70 20 mg dissolved in methylene chloride 0.5 ml. By introducing nitrogen gas into the solution at a room temperature, dissolved oxygen in the solution was removed out.

A polyurethane foam piece (an average pore size of 70 μm, semi-communicating pore structure; 10 cm × 10 cm × 7 cm, 700 cm$^3$) was soaked in the monomer solution and an excess amount of the solution was removed from the polyurethane foam by pressing and squeezing. The polyurethane foam piece was then applied into a glass vessel and allowed to stand under nitrogen atmosphere at 60° C. for 2 hrs for polymerization. The resulting polymer was washed with 50% acetone aqueous solution (50° C.) and then with distilled water for removing the remaining monomer and dioxane.

After replacing the distilled water by dioxane, dioxane solution 10 ml containing 2.0 g of 2-aminoethanethiol was added dropwise to the piece and incubated for aminolysis at 75° C. for 4 hrs. After the completion of the reaction, the polyurethane foam piece was thoroughly washed with 50% acetone aqueous solution and then with distilled water. An amount of the coating polymer was 12.5% by weight.

The monomer unit having the positively chargeable chemical moiety in the above polymer was methacrylic acid-2-mercaptoethylamino-2-hydroxypropyl with the CLOGP value of $-0.066$. Its estimated charge capacity, S/V value and porosity were about 1.71 meq/g, 146 $cm^2$/ml and about 77%, respectively.

EXAMPLE 3

A monomer solution was prepared by mixing diethyleneglycol methacrylate 7.0 g, dimethylaminoethyl methacrylate (the CLOGP value of 1.123) 2.51 g, glycerol dimethacrylate 0.50 g, tetrahydrofuran 21.0 g and an azo compound initiator V-65 20 mg. By introducing nitrogen gas into the solution at a room temperature, dissolved oxygen in the solution was removed out.

A polyurethane foam piece (an average pore size of 100 μm, semi-communicating pore structure; 10 cm×10 cm×7 cm, 700 $cm^3$) was soaked in the monomer solution and an excess amount of the solution was removed from the polyurethane foam by pressing and squeezing. The polyurethane foam piece was then applied into a glass vessel and allowed to stand under nitrogen atmosphere at 60° C. for 4 hrs for polymerization. The resulting polymer was washed with 50% acetone aqueous solution (50° C.) and then with distilled water for removing the remaining monomer and tetrahydrofuran. An amount of the coating polymer was 9.5% by weight.

Its estimated charge capacity, S/V value and porosity were about 1.32 meq/g, 117 $cm^2$/ml and about 81%, respectively.

EXAMPLE 4

A monomer solution was prepared by mixing polyethyleneglycol methacrylate PEG-200 7.0 g, diethylaminoethyl methacrylate (the CLOGP value of 1.188) 2.43 g, glycerol dimethacrylate 1.50 g, 75% tetrahydrofuran aqueous solution 18.0 g and the initiator V-65 20 mg. By introducing nitrogen gas into the solution at a room temperature, dissolved oxygen in the solution was removed out.

A polyurethane foam piece (an average pore size of 70μm, semi-communicating pore structure; MD Kasei Co.; 5 cm×5 cm×5 cm, 75 $cm^3$) was soaked in the monomer solution and an excess amount of the solution was removed from the polyurethane foam by pressing and squeezing. The polyurethane foam piece was then applied into a glass vessel and allowed to stand under nitrogen atmosphere at 60° C. for 4 hrs for polymerization. The resulting polymer was washed with 50% acetone aqueous solution (65° C.) and then with distilled water for removing the remaining monomer and tetrahydrofuran. An amount of the coating polymer was 6.7% by weight.

Its estimated charge capacity, S/V value and porosity were about 1.32 meq/g, 121 $cm^2$/ml and about 77%, respectively.

EXAMPLE 5

Cell culture was carried out by using the cell culture carriers prepared in EXAMPLE 1.

The cell culture carriers were thoroughly washed with distilled water which was then replaced successively by a phosphate buffer solution (PBS) and by DULBECCO's modified EAGLE medium which is auto-clavable (Nissui Pharmaceutical Co., Ltd.), and subjected to steam sterilization at 121° C. for 20 min.

Cells such as Vero cells (African green monkey kidney cells), MDCK cells (Mardain-Darby canine kidney cells), C cells (rat glial tumor cells), KN cells (human lung carcinoma cells), HeLa cells (human cervical epitheloid carcinoma cells) and WI-38 cells (human embryonic normal diploid cells) were cultured in e-RDF medium (Kyokuto Pharmaceutical Co., Ltd.) and the above DULBECCO's modified EAGLE medium both containing 10% fetal bovine serum (MITSUBISHI KASEI CORPORATION).

EXAMPLE 6

The cell culture carriers prepared in EXAMPLE 1 was added in petri dishes (6cm in diameter) in an amount of about 1.0 ml each, and the cell lines were cultured at 37° C. in a humidified incubator conditioned with a mixture of 5% $CO_2$ and 95% air. The cell density in each dish was as follows:

| | |
|---|---|
| Vero cells | $4.5 \times 10^7$ cells/ml; |
| HeLa cells | $8.5 \times 10^7$ cells/ml; |
| C cells | $8.1 \times 10^7$ cells/ml; |
| CHO-K/ cells | $6.8 \times 10^7$ cells/ml; |
| WI-38 cells | $1.2 \times 10^7$ cells/ml. |

EXAMPLE 7

The suspended culture was performed by using a spinner flask with a total volume of 1.0 1. The cell culture carrier pieces (0.5 mm×0.5 mm×0.5 mm; 5.0 ml) prepared in EXAMPLES 1, 2, 3 and 4, and sterilized were applied into each spinner flask. Serum 20.0 ml and the e-RDF medium were added to a final volume of 300 ml. Trypsinized Vero cells ($2.0 \times 10^7$) were inoculated into the above medium and the culture was carried out with a continuous stirring of 15 rpm. All of the cell culture carriers according to the present invention showed superior distensibility and growability of the cells and could attain the high-density cell culture.

EXAMPLE 8

To 100 ml of a phosphate buffer solution (pH 7.40) containing 0.1% bovine serum albumin (Sigma), the cell culture carriers prepared in EXAMPLES 1, 2, 3 and 4 as well as polyurethane piece ( 1.0 mm×1.0 mm×1.0 mm) uncoated with polymer as a control were added in an amount of 10.0 ml each and shaked at 37° C. for 5 hrs. Absorbance at 280 nm of each supernatant was then measured and an amount of the bovine serum albumin adsorbed by each polyurethane support was estimated. The results are shown in TABLE 3 below.

TABLE 3

| Carriers | adsorbing ratio (%) |
| --- | --- |
| EXAMPLE 1 | 0.1 |
| EXAMPLE 2 | 0.5 |
| EXAMPLE 3 | 0.0 |
| EXAMPLE 4 | 0.1 |
| Control | 12.5 |

EXAMPLE 9

A monomer solution was prepared by mixing diethyleneglycol methacrylate 7.00 g, dimethylaminoethyl methacrylate (the CLOGP value of 1.123) 2.50 g, glycerol dimethacrylate 0.50 g, 1-pentanol 22.0 g and the initiator V-65 20 mg. By introducing nitrogen gas into the solution at a room temperature, dissolved oxygen in the solution was removed out.

A part of the monomer solution was dropped onto 10 ml of porous ceramic carriers (an average pore size of 500 μm, porosity of about 85%; ceramic foam #30, BRIDGESTONE CORPORATION) and an excess amount of the solution was removed therefrom. The carriers were then applied into a glass vessel and allowed to stand under nitrogen atmosphere at 70° C. for 3 hrs for polymerization. The resulting ceramic carriers were washed with 50% acetone aqueous solution and then with distilled water for removing the remaining monomer and 1-pentanol. An amount of the coating polymer was 4.2% by weight.

Its charge capacity was estimated about 1.3 meq/g.

EXAMPLE 10

A monomer solution was prepared by mixing nonaethyleneglycol methacrylate 7.00 g, diethylaminopropyl methacrylate (the CLOGP value of 1.677) 2.50 g, nonaethyleneglycol dimethacrylate 0.50 g, 1-hexanol 20.0 g and the initiator V-65 50 mg. By introducing nitrogen gas into the solution at a room temperature, dissolved oxygen in the solution was removed out.

A part of the monomer solution was dropped onto 10 ml of porous ceramic carriers (an average pore size of 300 μm, porosity of about 80%; ceramic foam #40, BRIDGESTONE CORPORATION). Subsequently, the same procedures as in EXAMPLE 9 were performed.

An amount of the resulting coating polymer was 3.9% by weight. Its estimated charge capacity was about 1.2 meq/g.

EXAMPLE 11

A monomer solution was prepared by mixing tetraethyleneglycol methacrylate 7.0 g, glycidyl methacrylate 2.5 g, tetraethyleneglycol dimethacrylate 0.50 g, 1-hexanol 15.0 g and the initiator V-70 20 mg dissolved in methylene chloride 0.1 ml. By introducing nitrogen gas into the solution at a room temperature, dissolved oxygen in the solution was removed out.

A part of the monomer solution was dropped onto 10 ml of the porous ceramic carriers #40 (BRIDGESTONE CORPORATION) and an excess amount of the solution was removed therefrom. The carriers were then applied into a glass vessel and allowed to stand under nitrogen atmosphere at 50° C. for 2 hrs for polymerization. The resulting ceramic carriers were washed with 50% acetone aqueous solution and then with sufficient distilled water for removing the remaining monomer and 1-hexanol.

After replacing the distilled water by 1,4-dioxane, ethanolamine 0.50 g was added dropwise to the 10 ml of the carriers soaked in 1,4-dioxane and incubated for aminolysis at 50° C. for 4 hrs. After the completion of the reaction, the resulting carriers were thoroughly washed with distilled water. An amount of the coating polymer was 5.6% by weight.

The monomer unit having the positively chargeable chemical moiety in the above polymer was methacrylic acid-2-hydroxy-hydroxyethylaminopropyl with the CLOGP value of −0.669. Its charge capacity was estimated about 1.5 meq/g.

EXAMPLE 12

A monomer solution was prepared by mixing diethyleneglycol methacrylate 6.0 g, glycidyl methacrylate 3.0 g, glycerol dimethacrylate 1.0 g, 1-hexanol 18.0 g and the initiator V-70 20 mg dissolved in methylene chloride 0.1 ml. By introducing nitrogen gas into the solution at a room temperature, dissolved oxygen in the solution was removed out.

A part of the monomer solution was dropped onto 10 ml of polyurethane foam (an average pore size of 70 μm, porosity of about 77%, BRIDGESTONE CORPORATION) and an excess amount of the solution was removed therefrom. The carriers were then applied into a glass vessel and allowed to stand under nitrogen atmosphere at 50° C. for 2 hrs for polymerization. The resulting polyurethane foam carriers were washed with 50% acetone aqueous solution and then with distilled water for removing the remaining monomer, oligomer and 1-hexanol.

After replacing the distilled water by ethanol, 4-amino-1-butanol 0.50 g was added dropwise to the above carriers and incubated for aminolysis at 60° C. for 4 hrs. After the completion of the reaction, the resulting carriers were thoroughly washed with 50% ethanol, distilled water and phosphate buffer solution (pH 7.40), successively. An amount of the coating polymer was 6.3% by weight.

The monomer unit having the positively chargeable chemical moiety in the above polymer was methacrylic acid-2-hydroxy-4-hydroxybutylaminopropyl with the CLOGP value of −0.596. Its charge capacity was estimated about 1.9 meq/g.

EXAMPLE 13

The cell culture carriers prepared in EXAMPLE 11 was thoroughly washed with 50 mM phosphate buffer solution (pH 9.5). A 0.5 ml of a phosphate buffer solution (pH 9.5) containing 0.5% gelatin (Sigma) was added dropwise to the carriers (10 ml) and shaked at 50° C. for 5 hrs so as to modify the gelatin. After the completion of the reaction, the modified gelatin was washed with a phosphate buffer solution (pH 7.4).

EXAMPLE 14

A stainless column (20 cm in diameter and 10 cm in length) was filled with pieces of the ceramic foam #40.

A monomer solution was prepared by mixing triethyleneglycol methacrylate 0.80 g, diethylaminoethyl methacrylate (the CLOGP value of 1.981) 3.20 g, 2-hydroxyacrylate 6.00 g, butyl acetate and the initiator V-70 20 mg dissolved in methylene chloride 0.1 ml. By introducing nitrogen gas into the solution at a room temperature, dissolved oxygen in the solution was removed out.

The monomer solution was poured into the column under nitrogen atmosphere and an excess amount of the monomers was removed therefrom. The column was then soaked in a water bath at 50° C. for 2 hrs for polymerization. After the completion of the reaction, the resulting carriers were washed with 50% acetone aqueous solution and with distilled water. An amount of the coating polymer was 3.1% by weight. Its charge capacity was estimated about 1.7 meq/g.

EXAMPLE 15

The cell culture was carried out by using the cell culture carriers prepared in EXAMPLES 9, 10, 11, 12 and 13, respectively.

The cell culture carriers were thoroughly washed with distilled water which was then replaced successively by PBS (−), and by the same DULBECCO's modified EAGLE medium (DMEM) as used in EXAMPLE 5 twice. The washed carriers were then subjected to steam sterilization at 121° C. for 20 min. The e-RDF medium, modified EAGLE medium (MEM) or DMEM+Ham F12 (1:1) containing 10% bovine fetal serum (MITSUBISHI KASEI CORPORATION) was used for the culture of the cells listed in TABLE 4 below.

TABLE 4

| Cells Lines | Strain | Type | medium |
|---|---|---|---|
| Vero (ATCC CCL-81) | Kidney (African green monkey) | Fibroblast | e-RDF |
| COS-1 (ATCC CRL-1650) | Kidney (African green monkey) | " | DMEM + Ham F12 |
| CPK | Kidney (pig) | " | e-RDF |
| BHK-21 (ATCC CCL-10) | Kidney (Body pyrian hamster) | " | " |
| CHO-K1 (ATCC CCL-61) | Ovary (Chinese hamster) | " | " |
| Don (ATCC CCL-16) | Lung (Chinese hamster) | " | DMEM + Ham F12 |
| MRC-5 (ATCC CCL-171) | Lung (human embryo) | " | MEM |
| HeLa (ATCC CCL-2) | Cervical Epitheloid Carcinoma Cell (human) | " | e-RDF |
| MDCK (ATCC CCL-34) | Kidney (Mardain-Darby canine) | " | " |
| NIH/3T3 (ATCC CRL-1658) | Connective Tissue (mouse) | Fibroblast | MEM |

The cell culture carriers (0.2–0.3 ml) and the culture medium containing 10% bovine fetal serum were added into each well of a 12-well culture plate, which was then incubated at 37° C. in a CO incubator. The cell density of each culture cell was measured after three-day culture. The results are shown in TABLE 5 below.

TABLE 5

| Cells | EX. 9 | EX. 10 | EX. 11 | EX. 12 | EX. 13 |
|---|---|---|---|---|---|
| Vero | good | good | good | very good | not good |
| COS-1 | good | good | good | very good | not good |
| CPK | good | good | good | good | not good |
| BHK-21 | very good | very good | good | very good | good |
| CHO-K1 | good | very good | good | very good | good |
| Don | good | good | good | very good | not good |
| MRC-5 | not good | not good | good | good | not good |
| HeLa | good | good | good | very good | not good |
| MDCK | good | very good | good | very good | good |
| NIH/3T3 | not good | not good | good | good | not good |

The cell density was measured as follows: The cell culture carriers adsorbing the cells were recovered and washed with PBS solution twice. The washed carriers were then soaked in a solution (pH 7.40) containing 0.25% trypsin and 0.02% EDTA, and incubated at 37° C. for about 10 min to 1 hr. A gentle stirring may be adopted in order to facilitate detachment of the culture cells from the carriers. The suspended cells thus obtained were collected and their number was counted by means of a hematocytometer or counting chamber.

The water-insoluble polymer for use in coating the porous support according to the present invention can be prepared from liquid monomers, i.e., the monomer solution. Accordingly, the surface of the porous support made of various materials can wholly coated with the water-insoluble polymer. If the coating polymer has no or little positively chargeable chemical moiety, such moiety may be introduced into the coating polymer after polymerization has been finished.

The present cell culture carriers have a high S/V value, that is, they have many pores which the culture medium may easily pass through. Accordingly, by using the cell culture carriers of the present invention, the high-density cell culture may be attained in any type of the cell culture such as those using a petri dish or roller bottle in a laboratory scale and even mass culture in an industrial scale so that many useful biological active substances such as protein, monoclonal antibody, vaccine and virus can be efficiently produced in these cultures.

What is claimed:

1. A cell culture carrier consisting of a porous support which is at least partially coated with a water-insoluble polymer containing (meth)acrylic acid ester and/or (meth)acrylamide and a cross-linking agent in such an amount that the content of units derived from the cross-linking agent is 1 to 50% by weight of the water-insoluble polymer, and having a positively chargeable chemical moiety of charge capacity 0.2 to 4.0 meq per gram of the water-soluble polymer on the polymer surface.

2. The cell culture carriers according to claim 1 wherein the support has an average pore size of from 10 μm to 500 μm and porosity of from 40 to 99% by volume.

3. The cell culture carriers according to claim 2 wherein the support has an average pore size of from 20 μm to 100 μm and porosity of from 60 to 95% by volume.

4. The cell culture carrier according to claim 1 wherein the (meth)acrylic acid ester has a CLOGP value of −1.5 to +2.0 and the cross-linking agent has a CLOGP value of −1.5 to +2.5.

5. The cell culture carrier according to claim 4 wherein the (meth)acrylic acid ester is one or more compounds selected form the group consisting of 2-hydroxyethyl (meth)acrylate, diethyleneglycol (meth)acrylate, triethyleneglycol (meth)acrylate, tetraethyleneglycol (meth)acrylate, octaethyleneglycol (meth)acrylate, polyethyleneglycol (meth)acrylate, glycerol (meth)acrylate and glycidyl (meth)acrylate.

6. The cell culture carrier according to claim 1 wherein the (meth)acrylamide has a CLOGP value of $-1.0$ to $+2.0$ and the cross-linking agent has a CLOGP value of $-1.5$ to $+2.5$.

7. The cell culture carriers according to claim 6 wherein the (meth)acrylamide is one or more compounds selected from the group consisting of (meth)acrylamide, N-hydroxyethyl (meth)acrylamide, N-diethyleneglycol (meth)acrylamide, N-polyethyleneglycol (meth)acrylamide, N-hydroxypropyl (meth)acrylamide and methyl (meth)acrylamide.

8. The cell culture carrier according to claim 4 or 6 wherein the cross-linking agent is one or more compounds selected from the group consisting of ethyleneglycol di(meth)acrylate, diethyleneglycol di(meth)acrylate, triethyleneglycol di(meth)acrylate, tetraethyleneglycol di(meth)acrylate, octaethyleneglycol di(meth)acrylate, polyethyleneglycol di(meth)acrylate, glycerol di(meth)acrylate, methylene bis(meth)acrylamide, ethylene bis(meth)acrylamide, and diethylene bis(meth)acrylamide.

9. The cell culture carrier according to claim 1 wherein the content of the units derived from the cross-linking agent is 2 to 20% by weight of the water-insoluble polymer.

10. The cell culture carrier according to claim 1 wherein a CLOGP value of a monomer having the positively chargeable chemical moiety is from $-1.5$ to $+2.0$.

11. The cell culture carrier according to claim 10 wherein the monomer having the positively chargeable chemical moiety is selected from the group consisting of N,N-diethylaminoethyl (meth)acrylate, N,N-diethylaminopropyl (meth)acrylate, N,N-dimethylaminoethyl (meth)acrylate, 2-hydroxyethylamino-2-hydroxypropyl (meth)acrylate, 3-hydroxypropylamino-2-hydroxypropyl (meth)acrylate, 4-hydroxybutylamino-2-hydroxypropyl (meth)acrylate, N,N-diethylamino-2-hydroxypropyl (meth)acrylate, N-methylhydroxyethylamino-2-hydroxypropyl (meth)acrylate, N,N-diethylaminoethylamino-2-hydroxypropyl (meth)acrylate, 2-mercaptoethylamino-2-hydroxypropyl (meth)acrylate, 2-aminoethylamino-2-hydroxypropyl (meth)acrylate, 3-aminopropylamino-2-hydroxypropyl (meth)acrylate, 4-aminobutylamino-2-hydroxypropyl (meth)acrylate, trimethylammonium-2-hydroxypropyl (meth)acrylate, aminoethylacrylamide, dimethylaminoethylacrylamide, diethylaminoethylacrylamide, dimethylaminopropylacrylamide and trimethylaminoethylacrylamide.

12. The cell culture carrier according to claim 1 wherein the charge capacity is from 0.7 to 2.0 meq per gram of the water-insoluble polymer.

13. The cell culture carrier according to claim 1 wherein an amount of the polymer coating is from 0.5 to 20% by weight of the total cell culture carrier.

14. The cell culture carrier according to claim 1 wherein the water-insoluble polymer is insoluble in an organic solvent, chemically and biologically stable and resistant to sterilization by an autoclaving.

15. The cell culture carrier according to claim 13 wherein the porous support is made of the material selected from a group consisting of polymer foam, cloth, wood, glass, ceramics and metals.

16. The cell culture carrier according to claim 15 wherein the porous support is made of polyurethane foam.

17. A method for the preparation of the cell culture carriers according to claim 1 comprising soaking the porous support in a monomer solution containing the (meth)acrylic acid ester and/or (meth)acrylamides, cross-linking agent and polymerization initiator, followed by the polymerization thereof.

18. The method according to claim 17 wherein the monomer solution further contains a diluent.

19. A method for the culture of cells comprising: culturing cells in the presence of a carrier according to claim 1 and a biologically acceptable medium.

20. The method according to claim 19 wherein the cells are anchorage-dependent.

* * * * *